(12) United States Patent
Alonso-Garcia et al.

(10) Patent No.: US 7,749,721 B2
(45) Date of Patent: Jul. 6, 2010

(54) IMMUNO ENZYMATIC QUANTIFICATION METHOD FOR CHOLESTEROL ESTER TRANSFERRING PROTEIN (CETP)

(75) Inventors: Ana Lucia Alonso-Garcia, Mexico City (MX); Jaime Mas-Oliva, Mexico City (MX)

(73) Assignee: Universidad Nacional Autónoma de México, Cuernavaca (MX)

( * ) Notice: Subject to any disclaimer, the term of this patent is extended or adjusted under 35 U.S.C. 154(b) by 646 days.

(21) Appl. No.: 10/149,378

(22) PCT Filed: Dec. 13, 2000

(86) PCT No.: PCT/MX00/00053

§ 371 (c)(1),
(2), (4) Date: Mar. 6, 2003

(87) PCT Pub. No.: WO02/32935

PCT Pub. Date: Apr. 25, 2002

(65) Prior Publication Data

US 2003/0186342 A1    Oct. 2, 2003

(30) Foreign Application Priority Data

Dec. 13, 1999    (MX) .................................. 9911575

(51) Int. Cl.
*G01N 33/53* (2006.01)
*C07K 14/435* (2006.01)
*C07K 7/08* (2006.01)

(52) U.S. Cl. .......................... 435/7.9; 530/324; 530/327

(58) Field of Classification Search ........................ None
See application file for complete search history.

(56) References Cited

U.S. PATENT DOCUMENTS

| 5,599,679 | A | * | 2/1997 | Baylink et al. ................ 435/7.9 |
| 5,604,105 | A | * | 2/1997 | Jackowski ................... 435/7.4 |
| 5,631,133 | A | * | 5/1997 | Hanahan et al. ................. 435/6 |
| 5,705,388 | A | * | 1/1998 | Couture et al. .............. 435/366 |
| 5,770,355 | A | | 6/1998 | Brocia |
| 5,801,015 | A | * | 9/1998 | Cottarel et al. ............. 435/69.1 |

FOREIGN PATENT DOCUMENTS

| WO | WO 96/39168 | * 12/1996 |
| WO | WO 99/20302 A | 4/1999 |

OTHER PUBLICATIONS

Harlow & Lane. Antibodies: A Laboratory Manual. Cold Spring Harbor Laboratory, Cold Spring Harbor, NY, 1988, pp. 72-77, 141-142, 153, 319, 321-323, 342-345, 353, 553, 555-587, 591-593, and 599.*
Willingham, "Conditional Epitopes: Is Your Antibody Always Specific?" (Oct. 1999) The Journal of Histochemistry & Cytochemistry vol. 47(10):1233-1235.*
Saito et al. "Epitope mapping for the anti-rabbit cholesteryl ester transfer protein monoclonal antibody that selectively inhibits triglyceride transfer" (1999) Journal of Lipid Research 40:2013-2021.*
Harlow and Lane, "Antibodies: A Laboratory Manual," Cold Spring Harbor Laboratory, 1988, Chapter 5, p. 76.*
Colman et al., Research in Immunology, 1994; 145(1): 33-36.*
Abaza et al. Journal of Protein Chemistry, vol. 11, No. 5, 1992, pp. 433-444.*
Lederman et al. Molecular Immunology 1991, 28: 1171-1181.*
Li et al. PNAS 77 (1980), 3211-3214.*
Zaid et al., Glossary of biotechnology and genetic engineering (1999), FAO Research and Technology Paper No. 7, Food and Agriculture Organization of the United Nations, at p. 207, entry for the term "secondary antibody", downloaded from http://www.fao.org/docrep/003/X3910E/X3910E22.htm on Jan. 8, 2007.*
Genomics and Proteomics Glossary, which defines "secondary antibody" as "An antibody that recognizes and binds a primary antibody" (downloaded from http://www.genprogmag.com/Glossary.aspx on Jan. 8, 2007.*
Merriam-Webster OnLine Dictionary, definitions for the terms "recognize" and "bind", downloaded from www.m-w.com on Jan. 10, 2007.*
Qiu et al. "Crystal structure of cholesteryl ester transfer protein reveals a long tunnel and four bound lipid molecules" Nat Struct Mol Biol. Feb. 2007;14(2):106-13. Epub Jan. 21, 2007.*
Harlow & Lane ("Antibodies: A Laboratory Manual", Cold Spring Harbor Laboratory, Cold Spring Harbor, NY, 1988, pp. 23-25, 72-77, 141-142, 153, 319, 321-323, 342-345, 353, 553, 555-587, 591-593, and 599.*
The Academic Press Dictionary of Science and Technology (definition for the term "polyclonal"; Oxford: Elsevier Science & Technology (1996); retrieved Oct. 22, 2008, from http://www.credoreference.com/entry/3144515/.*
Janeway et al. Immunobiology: the Immune System in Health and Disease (1999), Elsevier Science Ltd/Garland Publishing, New York, NY, Fourth Edition, pp. 34-35.*
Wolfe, S.L., Molecular and Cellular Biology, 1993, pp. 790-793.*
Bolaños-Garcia, V.M., et al., "Stability of the C-terminal peptide of CETP mediated through an (i, i+4) array," *Biochim. Biophys. Acta* 1384:7-15, Elsevier Science B.V. (1998).
Brown, M.L., et al., "Molecular basis of lipid transfer protein deficiency in a family with increased high-density lipoproteins," *Nature* 342:448-451, Nature Publishing Company (1989).

(Continued)

*Primary Examiner*—Mark L Shibuya
*Assistant Examiner*—Christine Foster
(74) *Attorney, Agent, or Firm*—Sterne, Kessler, Goldstein & Fox P.L.L.C.

(57) ABSTRACT

The invention relates to an immunoenzymatic method for the quantification of protein CETP in plasma, which requires the utilization of fusion protein GST/CETP, the synthetic peptide CETP 11486-S496 and polyclonal antibody anti-CEPT 11486-S496. The method is used in the study of pathologies involving alterations in the CETP levels in plasma or in seric lipids and makes it possible to detect, evaluate and follow-up patients suffering from dyslipidemia and/or risk of altergenesis.

24 Claims, 2 Drawing Sheets

OTHER PUBLICATIONS

Bruce, C., et al., "Plasma Lipid Transfer Proteins, High-Density Lipoproteins, and Reverse Cholesterol Transport," *Annu. Rev. Nutr.* 18:297-330, Annual Reviews (1998).

Busch, S. J., et al., "Human Hepatic Triglyceride Lipase Expression Reduces High Density Lipoprotein and Aortic Cholesterol in Cholesterol-fed Transgenic Mice," *J. Biol. Chem.* 269:16376-16382, The American Society for Biochemistry and Molecular Biology, Inc. (1994).

Inazu, A., "Alternative Splicing of the mRNA Encoding the Human Cholesteryl Ester Transfer Protein," *Biochemistry* 31:2352-2358, American Chemical Society (1992).

Jeong, N. W., et al., "Production of Specific Antibodies against Human an Cholesteryl Ester Transfer Protein Using C-Terminal Active Peptide Obtained by Fusional Expression of Cholesteryl Ester Transfor Protein cDNA," *Mol. Cells* 4:529-533, The Korean Society for Molecular Biology (1994).

Jiang, X.C., et al., "Mammalian Adipose Tissue and Muscle are Major Sources of Lipid Transfer Protein mRNA," *J. Biol. Chem.* 266:4631-4639, The American Society for Biochemistry and Molecular Biology, Inc. (1991).

Jiang, X-C., et al., "Point Mutagenesis of Positively Charged Amino Acids of Cholesteryl Ester Transfer Protein: Conserved Residues within the Lipid Transfer/Lipopolysaccharide Binding Protein Gene Family Essential for Function," *Biochemistry* 34:7258-7263, American Chemical Society (1995).

Kondo, I., et al., "DNA polymorphism at the locus for human cholesteryl ester transfer protein (CETP) is associated with high density lipoprotein cholesterol and apoliporotein levels," *Clin. Genet.* 35:49-56, Munksgaard International Publisher, Ltd. (1989).

Marotti, K.R., et al., "Severe atherosclerosis in transgenic mice expressing simian cholesteryl ester transfer protein," *Nature* 364:73-75, Nature Publishing Company (1993).

Matsunaga, A., et al., "Detection of a point mutation in cholesteryl ester transfer protein gene by polymerase chain reaction-mediated site-directed mutagenesis," *Biochim. Biophys. Acta* 1166:131-134, Elsevier Science Publisher B.V. (1993).

Mezdour, H., et al., "Two-Site Enzyme Immunoassay of Cholesteryl Ester Transfer Protein with Monoclonal and Oligoclonal Antibodies," *Clin. Chem.* 40:593-597, American Association for Clinical Chemistry (1994).

Nagashima, M., et al., "Cloning and mRNA tissue distribution of rabbit cholesteryl ester transfer protein," *J. Lipid Res.* 29:1643-1649, Lipid Research, Inc. (1988).

Quinet, E., et al., "Inhibition of the Cellular Secretion of Cholesteryl Ester Transfer Protein by a Variant Protein Formed by Alternative Splicing of mRNA," *J. Biot. Chem.* 268:16891-16894, The American Society for Biochemistry and Molecular Biology, Inc. (1993).

Ritsch, A., et al., "Polyclonal antibody-based immunoradiometric assay for quantification of cholesteryl ester transfer protein," *J. Lipid Res.* 34:673-679, Lipid Research, Inc. (1993).

Roy, P., et al., "Structure-function relationships of human cholesteryl ester transfer protein: analysis using monoclonal antibodies," *J. Lipid Res.* 37:22-34, Lipid Research, Inc. (1996).

Rye, K-A., et al., "The Influence of Cholesteryl Ester Transfer Protein on the Composition, Size, and Structure of Spherical, Reconstituted High Density Lipoproteins," *J. Biol. Chem.* 270:189-196, The American Society for Biochemistry and Molecular Biology, Inc. (1995).

Sumikawa, K., et al., "Expression of Neurotransmitter Receptors and Voltage-Activated Channels from Brain mRNA in *Xenopus Oocytes*," *Methods in Neurosciences* 1:30-45, Academic Press (1989).

Swenson, T.L., et al., "Mechanism of Cholesteryl Ester Transfer Protein Inhibition by a Neutralizing Monoclonal Antibody and Mapping of the Monoclonal Antibody Epitope," *J. Biol. Chem.* 264:14318-14326, The American Society for Biochemistry and Molecular Biology, Inc.(1989).

Tall, A., "Plasma Lipid Transfer Proteins," *Annu. Rev. Biochem.* 64:235-257, Annual Reviews Inc. (1995).

Wang, S., et al., "Defective Binding of Neutral Lipids by a Carboxyl-terminal Deletion Mutant of Cholesteryl Ester Transfer Protein," *J. Biol. Chem.* 270:612-618, The American Society for Biochemistry and Molecular Biology, Inc. (1995).

Wang, S., et al., "Point Mutagenesis of Carboxyl-terminal Amino Acids of Cholesteryl Ester Transfer Protein," *J. Biot. Chem.* 268:1955-1959, The American Society for Biochemistry and Molecular Biology, Inc. (1993).

Wang, S., et al., "Identification of a Sequence within the C-terminal 26 Amino Acids of Cholesteryl Ester Transfer Protein Responsible for Binding a Neutralizing Monoclonal Antibody and Necessary for Neutral Lipid Transfer Activity," *J. Biol. Chem.* 267:17487-17490, The American Society for Biochemistry and Molecular Biology, Inc. (1992).

International Search Report for International Application No. PCT/MX00/00053, European Patent Office, Netherlands, mailed on Jun. 15, 2001.

\* cited by examiner

A)    B)    C)

IMMUNO ENZYMATIC QUANTIFICATION METHOD FOR CHOLESTEROL ESTER TRANSFERRING PROTEIN (CETP)

FIELD OF THE INVENTION

This invention is related to laboratory tests designed to identify and quantify the cholesterol ester transferring protein (CETP) in both biological and synthetic samples for clinical use, with the purpose of evaluating risk of atherogenesis and for use in research related to CETP.

BACKGROUND

In the 1970's, a definitive correlation was established between the levels and types of lipoproteins and heart disease. It has been observed that high levels of low density lipoproteins (LDL) can cause an increase in the incidence of heart disease, and that delay in the removal of these particles increases the time they remain in the plasma, exposes them to structural modifications and increases their interaction with the arterial walls. Furthermore, alterations in Apo B reduce the capacity of these particles to bind to their receptors and they are therefore largely recognized by macrophage receptors. The incapacity of the macrophages to regulate the internalization of modified LDL causes an accumulation of cholesterol esters and the formation of foam cells, a phenomenon that favors the development of atherogenesis.

Atherosclerosis is a phenomenon that begins in childhood and adolescence and progresses throughout life. Its consequences, such as arterial occlusion and its will known clinical manifestations (acute myocardial infarction, cerebral vascular accidents, gangrene of the lower limbs, etc.) begin many years before they are detected with the alteration of the vascular walls. Some patients who present serumal lipid levels that are higher than normal, also present a greater incidence of this type of ailment, as is the case of diabetics, nephropaths or congenital hyperlipidemics, among many others. In order to detect the possibility of these patients developing atherosclerosis and its clinical manifestations, the so-called "Coronary Risk Factors" are evaluated. These factors indicate the degree of exposure of the individual to circumstances that may determine a greater risk of presenting ailments related to this possibility; that is, they are used to determine the risk of atherogenesis. Coronary risk factors are as follows:

High low density total cholesterol and lipoproteins
High blood pressure
Smoking
Diagnosis of ischemic cardiopathy
Hypoalphalipoproteinemia (Low levels of high density lipoproteins or HDL)
Diabetes
Obesity
Family history of premature heart disease
Masculine sex
Proteinuria
Hypertriglyceridemia In order to establish if the patient is exposed to coronary disease risk factors, directed interrogations, exploration, determination of the lipid profile, electrocardiogram and radiograph of the thorax are performed. When peripheral vascular insufficiency is suspected, a Doppler Ultrasound and arteriography are included.

All the elements considered in this evaluation are used in the detection and follow-up of patients who are within the so-called "risk groups", which include individuals, who due to different pathologies, show one, some are all of the coronary risk factors. However, there is a large number of persons at risk from atherogenesis who have not been detected as they do not yet present the related clinical manifestations and therefore have not been placed within the risk groups. As there is no early diagnosis of these individuals, many valuable years of prevention are lost and when clinical manifestations do present themselves, the damage is mainly irreversible.

Furthermore, studies that assess atherogenesis risk factors based on the concentration of lipoproteins in the plasma of subjects included in some of the risk groups are inconsistent. Then, there are patients who are included in the risk groups who do not present the typical clinical description that denotes risk of atherogenesis, such as painless development with only a sensation of fatigue and lack of air, and some others go by unnoticed as they are confused with various pathologies. Hence, it is necessary to broaden the examination of the patient in the search for atypical manifestations.

There are also cases in which even when individuals are exposed to risk factors they do not develop atherosclerosis. Not all the factors to be assessed to determine the risk of atherogenesis are reliable. Some of the most widely discussed ones are included in the lipid profile, such as the high levels of total cholesterol and LDL and low levels of HDL in the blood, which are used to calculate the atherogenic index. This index is an arbitrary parameter that has experimentally proved to be unreliable in evaluating risk of atherogenesis: For example, in tests with rabbits submitted to diets high in cholesterol for long periods of time, high levels of total cholesterol, free cholesterol, esterified cholesterol and cholesterol associated with LDL, low levels of HDL associated cholesterol, hypertriglyceridemia, a high percentage of esterification and a high atherogenic index were obtained; however, they did not present atherogenesis.

In conclusion, the method for evaluating risk of atherogenesis used at present has severe limitations; first, the size and type of population likely to be evaluated is limited, due to the cost in time and money that is implied in carrying out the diagnosis tests and this makes the early detection of individuals at risk of atherogenesis who are not placed in risk groups difficult, therefore prevention of its complications is deficient. Second, even when the diagnosis parameters used at present allow certain certainty, most of them are qualitative and some of the quantitative parameters, the most important ones, are under discussion and it is therefore only possible to speak of a "high clinical suspicion of risk of atherosclerosis" since the results are not completely reliable. Third, not much is known about the homeostasis of lipids in humans and in mammals in general and it has not been possible to establish a clear relationship between many of the parameters considered as atherogenesis risk factors and their clinical manifestations, hence the determination of said risk cannot lie on solid bases, without a true understanding of the factors intervening in atherogenesis and their clinical manifestations.

There are other factors that can be useful in establishing the risk of atherogenesis in a more reliable way, such as the determination of the levels of the cholesterol ester transferring protein (CETP) in the plasma. This protein has been widely studied and is one of the best known factors intervening in lipid homeostasis. CETP has an important role in lipoprotein metabolism and in the development of arterial coronary disease, since it tends to generate high levels of LDL and VLDL that are associated with the progression of atherosclerosis (Marotti-K R, Castle-C K, Boyle-T P, Lin-A H, Murray-R W and Melchior-G W, 1993, *Nature* 364(6432):73-5). CETP is a multifunctional protein that promotes the exchange of cholesterol esters between HDL and LDL and the exchange of cholesterol esters and triacylglycerols between HDL and VLDL; its effect on the catabolism of HDL has an influence on its cholesterol ester content as well as on its composition, size and spherical structure (Rye-K A, Hime-N J & Barter-P J, 1995, *J. Biol. Chem.* 270(1):189-196) (Bruce-C, Chouinerd-R A y Tall-A R, 1998, *Annu. Rev. Nutr.* 18:297-330).

CETP also participates in the recycling of cholesterol deposited in the peripheral tissues during lipolysis of the lipoproteins (Jiang-XC, Moulin-P, Quinet-E, Goldberg-I J, Yacoub-L K, Agellon-L B, Compton-D, Schnitzer-Polokoff-R and Tall-A R, 1991, *J. Biol. Chem.* 266(7):4631-9) (Nagashima-M, McLean-J and Lawn-R, 1988, *J. Lipid. Res.* 29:1643-1649) (Tall-A, 1995, *Annu. Rev. Biochem.* 64:235-257). This transport, which we call "cholesterol reverse transport" confers on CETP the character of an anti-atherogenic protein, hence its importance in susceptibility or resistance to atherosclerosis (Kondo-I, Berg-K, Drayna-D, Lawn-R, 1989, *Clin. Genet.* 35(1): 49-56) (Bruce-C, Chouinerd-R A y Tall-A R, 1998, *Annu. Rev. Nutr.* 18:297-330). In accordance with the above, the factor that determines its anti-atherogenic capacity is not the level of HDL in plasma, but the distribution of sizes of its population, which has a strong correlation with CETP levels (Brown-M L, Inazu-A, Hesler-C B, Agellon-L B, Mann-C, Whitlock-M E, Marcel-Y L, Milne-R W, Koizumi-J, Mabuchi-H, 1989, *Nature* 342(6248):448-51).

In experimental work, it has been observed that mammal species lacking CETP in a normal way are resistant to developing arterial heart disease.

In contrast, in transgenic individuals of these same species that express CETP a decrease in size and HDL levels can be observed. As a consequence, CETP expression increases susceptibility to suffer from diet induced arterial heart disease (Rye-KA, Hime-NJ & Barter-PJ, 1995, *J. Biol. Chem.* 270 (1):189-196). Similarly, it has been observed that humans with a genetic deficiency of CETP present HDL levels that are much higher than the levels of normal subjects (hypoalpha-lipoproteinemia). These individuals seem to have a lower incidence of heart disease (Inazu-A, Quinet-E M, Wang-S, Browun-M L, Stevenson-S, Barr-M L, Moulin-P and Tall-A R, 1992, *Biochemistry* 31(8):2352-8). However, transgenic mice with hypertriglyceridemia that express CETP are protected against atherogenesis (Homanics-G E, de Silva-H V, Osada-J, Zhang-S H, Wong-H, Borensztajin-J and Maeda-N, 1995, *J. Biol. Chem.* 269:16376-16382).

This invention is related to laboratory tests designed to identify and quantify the cholesterol ester transferring protein (CETP) in both biological and synthetic samples for clinical use, with the purpose of evaluating risk of atherogenesis and for use in research related to CETP.

BRIEF SUMMARY OF THE INVENTION

In accordance with the above, the atherogenic or anti-atherogenic character of CETP is established in correlation with the HDL level and can act as atherogenic agent by increasing levels of low density lipoproteins, removing HDL cholesterol esters to incorporate them into LDL and VLDL. The anti-atherogenic character of CETP is based on its capacity to accelerate the transfer of cholesterol in the peripheral tissues to incorporate it in HDL, that is, counteracting the atherogenic effect through the "Reverse Transport of Cholesterol". We can therefore say that on evaluating CETP levels in correlation with the distribution of sizes and contents of cholesterol of the HDLs, its atherogenic or anti-atherogenic capacity can be established together with the risk of atherogenesis in all types of dyslipidemias. Based on the result of this test, it can be established if it is necessary or not to continue with the evaluation of the rest of the risk factors. Follow-up can also done of patients that have been diagnosed, evaluating the effectiveness of prevention programs or, where appropriate, the effectiveness of diets and/or treatments.

Even though there are references to other systems for the quantification of CETP in plasma, to date, given the nature of the equipment required, only methods whose technical complications restrict their use have been established. Such is the case of American U.S. Pat. No. 5,770,355, registered by Brocia, Robert W. In April 1998, entitled "Heart disease test kit and method of determining heart disease risk factor and efficacy of treatment for heart diseases". This patent requires the synthesis of an artificial particle and the use of cholesterol joined to a fluorescent molecule, which limits its use to laboratories that have the equipment necessary to measure fluorescence.

The reason for the present invention is to provide a system to detect and quantify CETP levels in biological and synthetic samples in a simple, fast way, that will make it possible to improve detection, diagnosis and follow-up of individuals at risk of atherosclerosis, with or without clinical manifestations related to this is pathology, and that may or may not be included in risk groups. This will be done through the incorporation of this system into protocols and equipment routinely used in human and veterinary clinical laboratories.

DESCRIPTION OF THE SEQUENCES

Figure 1:
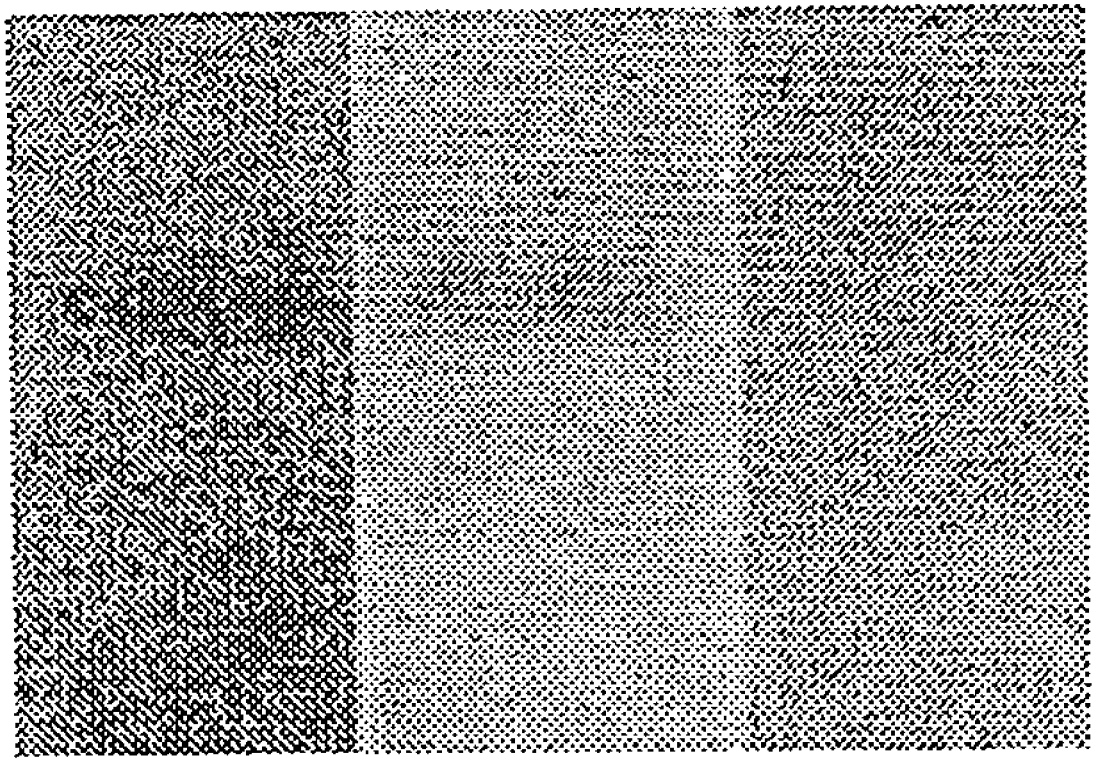
FIG. 1. Western-Blot type tests using the polyclonal antibody Anti-CETP H486-S496 against human plasma (lane A) and rabbit plasma (lane B). The polyclonal antibody Anti-CETP H486-S496 recognizes the CETP of ~67 KDa. In tests with raw extracts depleted of lipids and perfused tissues exactly the same result was obtained. In order to discard the possibility of false positives in which the antibody recognizes albumin in plasma, controls against BSA (lane C) were included in all the tests. The result of these controls is negative, therefore the polyclonal antibody recognizes CETP specifically.

SEQ ID NO: 1 Sequence. Sequence of sense oligonucleotides, compatible with the antisense oligonucleotide with SEQ ID NO: 2 sequence in PCR amplifications. It corresponds to the sequence from bases 1391 to 1414 in exon 15 of CETP mRNA. It is 24 nt long, G-C content 45.8%, fusion temperature 55.9° C.

SEQ ID NO: 2 Sequence. Antisense oligonucleotide sequence, compatible with the sense oligonucleotide with SEQ ID NO:1 sequence, in PCR amplifications. It is complementary to the sequence from bases 1852 to 1828 in exon 16 of CETP mRNA. It is 25 nt long, G-C content 48.0% fusion temperature 55.3° C.

SEQ ID NO: 3 Sequence. Nucleotide sequence of the CETP fragment recovered from the clone pMosBlueICETP3' and subcloned in pGex-2T, generating clone pGex-2T/CETP3'. On subcloning the CETP fragment, three nucleotide of the pMos vector (underlined) are transported in such a way that the clone pGex-2T/CETP3' includes these nucleotide between the region coding for GST and the one coding for CETP.

ID-4 Sequence. Amino acid sequence corresponding to the CETP section in recombinant protein GST/CETPCOH, coded by clone pGex2T-CETP 3'. This sequence corresponds to the last 33 residues of its carboxyl terminal, from I464 to S496, among which the residues F481, L488, F491 and L495 are included, which are important for maintaining cholesterol ester transfer activity (Tall-A, 1995, Annu. Rev. Biochem. 64:235-257). This epitope has a high content of alpha helix structure and includes the whole cholesterol ester binding motif (from G473 to S496) (Matsunaga-A, Araki -K, Moriyama-K, Handa-K, Arakawa-F, Nishi-K, Sasaki-J and Arakawa-K, 1993, Biochim. Biophys. Acta. 1166(1):131-4) (Wang-S, Wang-X, Deng-L, Rassart-E, Milne-RW, Tall-AR, 1993, J. Biol. Chem. 268(3):1955-9. The molecular weight (M.W.), isoelectric point (I.P.) and charge to pH7 were obtained with the help of the DNAstar program (Lasergene).

SEQ ID NO: 5 Sequence. Sequence of the synthetic CETP peptide H486-S496, designed for the production of the polyclonal antibody IgY Anti-CETP H486-S496. This peptide has a cysteine residue in the amino end that is used to join it to the transporting protein. The secondary structure was reported by Tall-A (1995), Annu. Rev. Biochem. 64:235-257 and confirmed by us with Chou-Fasman and Gamier-Robson algorithms. The peptide includes three of the four residues that are of special importance for conserving binding capacity to neutral lipids, these are F481, L488, F491 and L495. The molecular weight (M.W.), isoelectric point (P.I.) and charge to pH7 data were obtained with the help of the DNAstar program (Lasergene); the pH value with which the peptide becomes soluble in water was obtained experimentally.

DETAILED DESCRIPTION OF THE INVENTION

This invention consists of a system to detect and quantify CETP. The system requires the use of fused protein GST/CETPCOH, synthetic peptide CETP H486-S496 and polyclonal antibody H486-S496. The use of this system makes it possible to identify, evaluate and give follow-up to patients with dyslipidemias, whose effects are related to alterations in the level of CETP circulating in plasma with the purpose of evaluating their risk of developing atherosclerosis. This system is designed for use in clinical practice and/or research related to CETP. Samples of different origins, both biological and synthetic, can be used, preferably plasma or serum, cellular extracts or from tissues, culture media and purified or semi-purified antigens.

Fused Protein GST/CETPCOH

GST/CETPCOH has an approximate weight of 67 KDa, 3.7 KDa correspond to the CETP carboxyl terminal, the rest correspond to glutathione-S transferase. GST/CETPCOH is designed for use in both ELISA and Western-Blot tests, as a standard that permits the identification and quantification of CETP through the use of antibodies directed specifically against their carboxyl terminal.

The sequence of the section corresponding to CETP, in the fused protein GST/CETPCOH is presented as an ID-4 sequence. This covers the last 33 residues of the CETP carboxyl terminal, from I464 to S496, and has a high content of alpha helix structure and includes the whole cholesterol ester binding motive (from G473 to S496). In the design of the standard for the ELISA and Western-Blot tests, the CETP carboxyl end was chosen because it includes F481, L488, F491 and L495 residues and it has been experimentally demonstrated that these residues are of special importance for maintaining the cholesterol ester transfer activity (Wang-S, Kussie-P, Deng-L and Tall-A, 1995, J. Biol. Chem 270(2): 612-618), (Jiang-X, Bruce-C, Cocke-T Wang-S, Boguski-M and Tall-A, Biocem. 34:7258-7263). (Matsunaga-A, Araki-K, Moriyama-K, Handa-K, Arakawa-F, Nishi-K, Sasaki-J and Arakawa-K, 1993, Biochim. Biophys. Acta. 1166(1): 131-4) (Wang-S, Wang-X, Deng-L, Rassart-E, Milne-R W, Tall-A R, 1993, J. Biol. Chem. 268(3):1955-9). In this way, the quantification of CETP will have as standard only the CETP carboxyl that includes the sites necessary for maintaining its binding capacity to cholesterol esters.

Another of the advantages of using this standard is that it does not require the purification of CETP from natural sources. Purification of the recombinant protein is simpler and faster than purification of CETP from plasma; a greater amount of recombinant protein can be obtained from bacterial cultures than CETP from plasma; the purity of recombinant preparations is greater than that of purifications of plasma, and greater purity reduces the risk of false positives and erroneous quantifications. The generation of recombinant proteins can be done under controlled conditions unlike those that occur in biological samples that depend on a large amount of variables and most of these cannot be controlled. Finally, the recombinant protein only includes the carboxyl end, and therefore it not only avoids a cross reaction against other proteins but against other CETP epitopes as well.

Design of Synthetic Peptide CETP H486-S496 and the Obtaining of Polyclonal Antibody Anti-CETP H486-S496.

The CETP detection and quantification system requires the use of an antibody specifically directed against the neutral lipids binding site in order to guarantee that only the CETP conserving this epitope will be detected and that therefore conserves the capacity to bind to neutral lipids, including cholesterol esters. We must add here that until now a large of mutations and alternative editions of cholesterol esters have been reported most of which do not translate or translate into proteins that do not secrete plasma. Only one of these CETP variations, depleted from exon nine (CETPΔ9), is poorly secreted into the extracellular medium (Quinet-E, Yang-T P, Marinos-C and Tall-A1993, J. Biol. Chem 268(23):16891-16894).

Although this CETPΔ9 version is inactive in lipid transfer, it conserves the neutral lipid binding epitope and therefore is potentially detectable by antibody Anti-CETP H486-S496; however, it is known that it is poorly secreted into the extracellular medium and there are no reports of its presence in plasma, hence its effect on CETP quantification using this system will be minimum or nil.

However, during research prior to this document, we found another version of CETP without the cholesterol esters binding motif (CETPAΔ16) and therefore without a neutral lipid binding capacity. This version of CETPAΔ16 can be found in large quantities in the plasma and could be detected by antibodies directed against any epitope of the original version of CETP, except for antibodies directed against the cholesterol ester binding motif.

Given the above, the antibody generated for this system should not recognize quantification of the CETPΔ16 variety, furthermore, it should avoid generating antibodies against any other protein present in mammal plasma and against any other CETP epitope; it is also a safety measure that avoids false positives and erroneous quantifications. For this reason, it was discarded as an antigen to complete, purified CETP of any mammal species and instead a synthetic peptide was designed as antigen. A synthetic peptide can be obtained with a high degree of purity and, depending on its design, it permits the generation of antibodies against a specific epitope.

In order to design this peptide, the RT-PCR product, amplified with a pair of oligonucleotides with SEQ ID NO: 1: and SEQ ID NO: 2: sequences, was sequenced. This sequence was translated to an amino acid sequence and analyzed with the help of the DNAstar program (Lasergene), from which the prediction of the Kyte-Doolittle type hydrophobicity index and the secondary structure were obtained with the Chou-Fasman and Garnier-Robson alrogithms.

Based on this information and on the characteristics required for this CETP quantification system, we designed the synthetic peptide, taking into account the following considerations:

It must be included within the neutral lipid binding motive. That is, among the last 26 residues of the CETP carboxyl (Wang-S, Deng-L, Milne-R S and Tall-A R, 1992, *J. Biol. Chem.* 267(25):17487-17490). In this way, the antibody can only recognize the CETP version that includes this epitope.

It must include the greatest possible number of residues reported as important to maintain lipid binding capacity. F481, L488, F491 and L495 residues important in the cholesterol ester transfer activity are included among the 26 amino acids of the lipid binding motive (Tall-A, 1995, *Annu. Rev. Biochem.* 64:235-257). With this, we not only focused recognition of the antibody against the neutral lipid binding motive but also against the residues that are most important in maintaining this capacity.

Its sequence does not have homology with other CETP epitopes or other proteins expressed in mammals or hens. Although antibodies can be obtained using any animal model that does not express CETP in order to obtain the adequate antibody for this system, hens are preferably used and in this way a strong immune response due to the phylogenetic difference is ensured. For this reason, peptide design must not permit homology with proteins expressed in hens. On the other hand, the antibody must recognize CETP only and only in an epitope, therefore the synthetic peptide should not have homology with other proteins or with any other CETP epitope.

Its size must permit the smallest possible number of recognition windows by the immune system. A peptide that fulfils this condition permits the generation of polyclonal antibodies that recognize specific epitopes with the same or greater precision than a monoclonal antibody.

It must have a cysteine residue in its amino end in order to direct its binding to the transporting protein. A cysteine residue in the amino end of the peptide makes it possible to direct its binding to a transporting protein so that all recognition windows for the immune system are exposed.

It must be in a region whose immune response has been proved. In earlier works, it was demonstrated that the carboxyl end of human CETP generates an immune response obtaining a monoclonal antibody against this motif (Swenso-T, Hesler-C B, Browun-M L, Quinet-E, Trotta-P P, Haslanger-M F, Gaeta-F C, Marcel-y l, Miline-R W and Tall-A R, 1989, J. Biol. Chem. 264:14318-14326). However, the recognition windows of this antibody have not been determined within the 26 amino acids that comprise this epitope. Due to the above, we could not discard the possibility of there existing non antigenic windows in this epitope and that one of them could coincide with the synthetic peptide sequence that we designed, and therefore our design was experimentally proved.

In accordance with the above, we designed synthetic peptide CETP H486-S496 whose sequence is shown as ID-5 sequence and that has the following characteristics: The peptide sequence is found within the cholesterol ester binding motif and corresponds to the sequence of residues H486 to S496 of rabbit CETP; that is, the last eleven residues of the protein, and therefore it is unable to recognize the CETPAΔ16 version. Its sequence includes three of the four residues that are of special importance in maintaining the lipid binding union: L488, F491 and L495. The synthetic peptide sequence does not have homology with other CETP epitopes or with other mammal or hen proteins, in contrast it presents high homology with the carboxyl terminal of CETP of several species: 100% with the rabbit, human and monkey and 90% with the hamster. Since the peptide is made up of only eleven residues, it presents only one recognition window to the immune system. A cysteine residue was added to the original CETP sequence in order to direct binding to the transporting protein. The antigenic capacity of the synthetic peptide CETP H486-S496 was demonstrated through obtaining polyclonal antibody Anti-CETP H486-S496.

In order to obtain polyclonal antibody Anti-CETP H486-S496, peptide CETP H486-S496 was joined to the KLH transporting protein. KLH was used instead of bovine serum albumin in order to avoid the generation of antibodies that would recognize the albumin present in plasma, which would give rise to false positives and erroneous quantifications in the test results. Antibodies are obtained in model animals, preferably LEGHORN white hens, that are subcutaneously inoculated once a week using a standard 63 day protocol. The titer of the antibodies in the plasma is determined using the ELISA technique. The ages in the eggs are isolated. In the case of using other model animals IgGs in the plasma are isolated. Although this antibody can be obtained from several model animals that do not express CETP, the titer in hens will be much higher.

It should be pointed out that due to the design of the synthetic peptide used as antigen, the polyclonal antibody generated for this system exclusively recognizes H486 to S496 residues within the cholesterol ester binding motive. This epitope includes three of the four residues that are of special importance in maintaining the lipid binding capacity: L488, F491 and L495. Furthermore it only has one recognition window and therefore has greater precision than the monoclonal antibody mentioned above. According to the design of the antigen and the experimental tests of the antibody, it does not recognize the CETPΔ16 version, other mammal or hen proteins or other CETP epitopes; nevertheless it can recognize the CETP of other species since the region chosen in the design of the antigen is highly conserved in several species of mammals.

Cross reaction tests were performed using ELISA and Western Blot techniques against the free and joined synthetic peptic, the recombinant protein GST/CETPCOH and bovine serumal albumin; with this the specificity of the antibody for its antigen was determined. As well as in the use of ELISA and the Western-Blot, this antibody could be used in the future in therapy protocols in patients with dyslipidemia, associated with CETP levels in plasma as well as in CETP purification systems and other proteins with homologue sequences to the carboxyl in this one.

System For CETP Detection and Quantification

The objective of this system is to detect and quantify CETP in the largest number of samples possible in a simple, rapid way. To do so the classic ELISA (Enzyme-Linked Immunosorbent Assay) method is used. As standards in this test, the recombinant protein GST/CETPCOH and/or synthetic peptide CETP H486-S496 is used. The control antigen as well as the samples to be quantified, preferably plasma or serum, are joined to the ELISA plate following the routine procedures of clinical laboratories.

If samples of plasma or serum are used, a sample of 20-5 pl is preferably required which does not need any previous treatment. The minimum level of detection of this system is 0.018 pM (1 pg) of CETP, the maximum level is 360 pM (20 µg). The standard curve suggested for human and rabbit plasma is:

| (pM/100 µL) |
|---|
| 0.250 |
| 0.166 |
| 0.125 |
| 0.100 |
| 0.083 |
| 0.071 |
| 0.062 |
| 0.055 |

An initial dilution of plasma or serum of 1:15,000, 100 µl per well is recommended. This dilution must be adjusted should the level of CETP in the sample exceed the limits of the curve.

Polyclonal antibody Anti-CETP H486-S496 is used as primary antibody to exclusively detect the motive responsible for the binding of neutral lipids to CETP in both standards and samples. Depending on the origin of the primary antibody, hen or mammal, the secondary antibody, preferably commercial, joined to peroxidase, Anti-IgY or Anti-IgG respectively, is chosen. In order to use the primary antibody in ELISA the preferable dilution is 1:5000. The secondary antibody must be preferably commercial, preferably joined to peroxidase, the dilution of the secondary antibody must be the one recommended by its manufacturer.

The maximum number of samples that can be handled by duplicate in each box is 39, in a protocol that includes the standard curve and a negative control. Experimentally, we have discarded false positives by means of the use of a combination of negative controls, but the negative control must be included in duplicate in order to consider the experimental error of the user of the system.

Since CETP is highly conserved in mammals, the system is able to recognize CETP in the plasma of species that express CETP in a natural way or of transgenic species with this gene, providing homology with the last 11 residues of the carboxyl terminal is conserved. For this reason, this system is used in human and veterinarian clinical work.

Kit For the Quantification of the Cholesterol Transferring Protein in Biological Samples The system described above is the basis for the design of a diagnostic kit, of use in determining CETP levels in a large number of samples that is quick and simple to use, and which does not exist to date. This kit is designed for clinical use, preferably using plasma or serum samples from species that express CETP in a natural way or transgenic species with this gene. They must conserve homology in the last 11 amino acids of the carboxyl end.

This kit can be easily adapted to samples of different origins, both biological and synthetic, for both the human or veterinarian clinical laboratory and for various research uses.

The kit is composed of:

Solutions
  PBS 10×
  Binding buffer, pH 9.6 50 mM($Na_2CO_3$ 35 mM+$NaCO_3$ 15 mM+$NaN_3$ 20 µg/ml)
  Phosphate-Citrate Buffer Phosphate of Na- Ac. Citric 0.05M, pH 5

Antigens
  Recombinant protein GST/CETPCOH
  Synthetic peptide CETP H486-S496

Antibody
  1st Antibody IgY or IgG Anti-CETP H486-S496

Procedure
1. The control antigen (GST/CETPCOH and/or CETP H486-S496) as well as the standard curve are diluted in 100 µl of binding buffer.
2. Join antigens and samples to the ELISA plate, incubating for 2 hrs at 37° C.
3. Remove the antigens and block with 200 µl of Ovoalbumin 0.5 mg/ml, in a carbonate buffer for 1 hr at 37° C. At the end of the incubation, wash four times with 0.1% PBS-Tween (PBST).
4. Incubate with 100 µl of Anti-CETP H486-S496, in a dilution of 1:5000 in PBST, for 1 hr, at 37° C. At the end of the incubation, wash four times with PBST.
5. Incubate with 100 µl of the secondary antibody joined to peroxidase, Anti-IgY or Anti-IgG, as the case may be, at the dilution recommended by the manufacturer in PBST. Incubate for 1 hr at 37° C. At the end of the incubation, wash four times with PBST and twice with $H_2O$.
6. Develop with 100 µl of substrate for peroxidase, preferably OPD, in the conditions recommended by the manufacturer.
7. Incubate for 20 min in darkness, stop the reaction with 50 µl of $H_2SO_4$ 1.5M to read at 490 nm.
  The whole procedure is done with the ELISA plate covered, avoiding temperature gradients.

By including CETP quantification among the parameters for diagnosing atherogenesis risk, the certainty of diagnosis is increased significantly, since it is a quantitative parameter that has been able to establish a clear relationship with many of the parameters considered as atherogenesis risk factors and their clinical manifestations. For this reason, in order to facilitate the implementation of this system in clinics, we designed the Kit described above. The ease of use of this kit permits its routine use in clinical practice, making it possible to identify individuals who have no clinical manifestations of atherosclerosis and do not fall within the risk groups. The foregoing facilitates the detection of individuals at risk of non-diagnosed atherogenesis or with atypical syndromes. It also facilitates the diagnosis and follow-up of patients and the evaluation of the effectiveness of the treatments they are given.

Comments

The tools generated in the development of this CETP quantification Kit can have different uses. The oligonucleotides with SEQ ID NO: 1: and SEQ ID NO: 2: sequences were designed for use in amplifications by PCR, however, they can also be used as molecular probes against DNA and PCR products containing their sequence. The oligonucleotide with SEQ ID NO: 2 sequence can also be used as a probe against the CETP messenger, but not the SEQ ID NO: 1 sequence oligonucleotide. Both can be tools in future work, in both research and in the treatment of patients with dyslipidemias, related to CETP expression.

The clones pMosBlue/CETP3' and pGex2T/CETP3' can also be used to obtain specific probes against DNA, mRNA and CETP RCR products. The clone pMosBlue/CETP3' can be used to subclone the cDNA fragment of CETP in other vectors for different purposes, from obtaining probes and other recombinant proteins to experimental protocols for the treatment of patients with dyslipidemias related to CETP. The clone pGex2T/CETP3' can also be used for subcloning and for obtaining recombinant protein GST/CETPCOH in large amounts and in a soluble form by means of a simple, cheap method.

Recombinant protein GST/CETPCOH is designed for use as standard in both ELISA and Western-Blot tests in clinical practice that permits the identification and quantification of CETP by means of the use of antibodies directed specifically against the carboxyl terminal. In Western-Blot type tests it is a positive standard and/or control that is easy to manage, that would not be possible with proteins or low weight peptides. The obtaining of this fused or recombinant protein provides a standard for the identification and quantification of CETP that is more reliable than those purified from natural sources. This recombinant protein also has applications in the research area, for example, in structure studies with high resolution systems such as crystallography of X-Rays; in activity studies since it contains the epitope that gives the capacity to bind to lipids; in affinity chromatography for the purification of antibodies or other molecules similar to the carboxyl terminal of CETP; in the production of antibodies against the CETP carboxyl, without the need to bind to transporting proteins, among many others.

The synthetic peptide CETP H486-S496, is useful not only for the production of antibodies and as a standard in the ELISA protocol, but it can also be an important tool in structure and activity studies.

The use of the CETP detection and quantification system makes it possible to identify, evaluate and give follow-up to patients with dyslipidemias, whose effects are related to alterations at the level of CETP circulating in the plasma, with the purpose of evaluating the risk of atherogenesis. This system will facilitate the handling of a large number of samples in a quick, simple way, permitting the routine use of this test in human and veterinary clinical laboratories and in this way the size of the population that can be evaluated is expanded. Although it preferably uses plasma or serum samples, it can also be adapted for use with cell or tissue extracts, culture media, purified or semi-purified antigens, etc., which enormously increases its field of use in research.

The use of the kit can be extended to research into the facts and phenomena involved in lipid homeostasis, as well as in the study of the physical, chemical and biological characteristics of CETP and molecules related to it, using samples obtained from experimental biological or non-biological models, preferably extracts of tissues, organs or cells in culture, culture media, recombinant proteins and synthetic peptides.

Examples Of Use

1.—Oligonucleotide Design:

Taking as model the New Zealand white rabbit (*Oryctolagus cuniculus*), total RNA from the liver was obtained using the method described by Sumikawa-K; Parker-I and Miledi-R (1989, *Methods in Neurosciences* 1:30-45), the RNA poly (A$^+$) fragment was isolated using chromatography in the oligo(dt)-cellulose method. cDNA was synthesized using the commercial system for RT-PCR (Perkin Elmer), using mRNA from the liver. For the RT-PCR protocol, a set of oligonucleotides was designed with the help of the Mac Vector program. The oligonucleotide design allows for the specific amplification of the 3' end of the cDNA of CETP, which is specially difficult given the characteristics of the cDNA sequence characteristics of CETP, the most determining of which is its high content of G-C (over 65%). As a result of the above, the following parameters were established in the design of the oligonucleotides used in the PCR protocol:

SEQUENCE: cDNA of rabbit CETP, published by Nagashima-M, McLean-J and Lawn-R in 1988 (*J. Lipid. Res.* 29:1643-1649).
SEQUENCE ANALYZED: from nucleotide 1 to nucleotide 1870.
SIZE OF OLIGONUCLEOTIDES: from 18 to 30 bases.
FUSION TEMPERATURE: 55-80° C.
G-C CONTENT: 45-55%.
PRODUCT SIZE: 400-1000 pb.
MAXIMUM COHERENCE NUMBER IN CONSECUTIVE BASES:
  Oligonucleotide Versus Oligonucleotide (any)=4.
  Oligonucleotide Versus Oligonucleotide (only G-C)=2.
  3' end versus 3' end=2.

No Restriction Sites Were Adapted Or Added.

This design allows only one option of sense oligonucleotides near to the 3' end and one of the antisense oligonucleotides that it is compatible with. The sequences in this set of oligonucleotides are shown as SEQ ID NO: 1 sequence (sense oligonucleotide) and SEQ ID NO: 2 sequence (antisense oligonucleotide). This set of oligonucleotides generates a product of 462 bp, from bases 1391 to 1852, that extends from the 3' end of exon 15 to the non-coding region of exon 16 of the CETP mRNA. The temperature for optimum alignment is 59.9° C., the percentage of G-C 60.4% and fusion temperature 83.2° C.

2.—Cloning the C-terminal End of CETP

The PCR product generated by this set of oligonucleotides was cloned in the pMosBlueT vector (Amersham). This strategy made it possible to integrate the BamHI and SmaI restriction sites to the PCR product in order to permit their subcloning in the pGex-2T expression vector (Pharmacia LKB Biothec), in the correct orientation and reading framework for the expression of the fused protein. In this way, two recombinant plasmids cloned with the 3' end of the cDNA of CETP, called clone pMosBlue/CETP3' and clone pGex-2T/CETP3', were generated.

The clone pGex-2T/CETP3' was transformed in the bacterial strain *Escherichia coli* DH5α, in order to obtain recombinant proteins fused to glutathion-S Transferase (GST). The transformed strain is cultivated for 8 hrs at 37° C., in 500 ml of Super Luria culture medium with 50 µg/ml of ampicillin added. Culture induction is conducted with 0.4 mM of IPTG for three hours. After incubation, the bacteria are mechanically lysed and the fused protein GST/CETPCOH is recovered in a Glutathion-Agarose column (SIGMA), using a known protocol (Smith-DB and Corcoran-LM, 1995, Expression and Purification of Glutathion-S Transferase Fusion Proteins. In Short Protocols in Molecular Biology [Ausbel-MF, Brent-R, KingstonRE, Moore-DDR, Seidman-JG and Strhl-K], WILEY, 3rd ed. pp16.18-16.31).

3.—Obtaining Antibodies of the IgY Anti-CETP Type

The peptides joined to KLH were used for the production of the antibodies, preferably in hens, using a standard 63 day protocol, inoculating them subcutaneously once a week. The inocula consisted of 200 µg BSA/200 µl PBS+200 µl of complete Freund adjuvant (Sigma Inmuno Chemicals) in the first application and 200 µg BSA/150 µl PBS+150 µl of incomplete Freund adjuvant (Sigma Inmuno Chemicals) in subsequent applications. The antibody titer in the plasma was determined by the ELISA technique. The IgYs were isolated from eggs collected over 2 weeks. Both the binding and the production of antibodies and titration using ELISA of the first plasma sample was done with ADI (Alpha Diagnostic International).

4.—Western-Blot Assay for the Detection of CETP

The conditions of use of the polyclonal antibody Anti-CETP H486-S496 were standardized in Western-Blot type tests against human and rabbit plasma and raw and depleted lipid extracts from perfused tissues. The primary antibody in 1:5,000 dilutions and the secondary antibody Anti-Chicken IgG, (H+L) conjugated with peroxidase (PIERCE) 1:10,000 were used. Both the blocks and the incubations were done with a 2.5% powdered skimmed mild suspension in 0.1% TBS-Tween at 37.degree. C., for 1 hr. Visualization was done with SuperSignal Substrate (PIRCE) in X-OMAT autoradiographic plates (Kodak), for the quantitative or qualitative determination of CETP. BSA was used as a negative control in these tests. In order to discard the possibility of the antibody unspecifically recognizing albumin, whose molecular weight is close to CETP (.about.67 KDa), negative controls with BSA were included. In all the tests run, antibody Anti-CETP H486-S496 specifically recognizes CETP. The results of these tests can be seen in FIG. 1.

5.—ELISA Assay For the Detection of CETP

Figure 2:
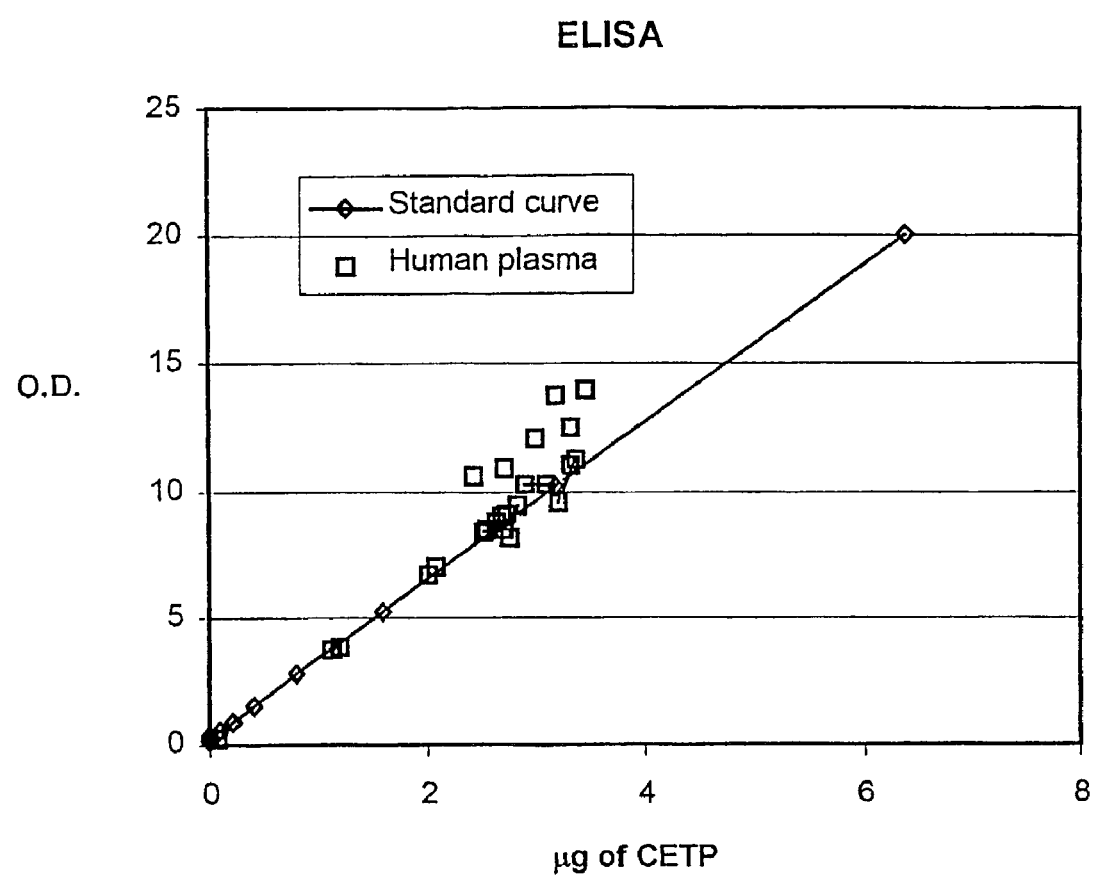
FIG. 2. This figure shows a graph whose standard curve values were obtained using synthetic peptide H486-S496 and the result of CETP quantification in 25 samples of human plasma. According to these results, CETP levels in the sample group are found between 2 to 3 µg/ml, which is the equivalent of 28-31 pM/ml. These results were obtained with this system of CETP quantification.

The conditions of use of polyclonal antibody Anti-CETP H486-S496 in ELISA tests against human and rabbit plasma were standardized. Primary antibody in dilutions of 1:2,000, and secondary antibody Anti-Chicken IgG, (H+L) conjugated with peroxidase (PIRCE) 1:2,000 were used. Both the blocks and the incubations were done with 0.1% PBS-Tween at room temperature for 1 hr. Visualization was done with OPD (o-Phenylenediamine Dihydrochloride, SIGMA). The O.D. readings were done at 450 nm. BSA was used as a negative control in these tests. In order to discard the possibility that the antibody unspecifically recognizes albumin, negative controls with BSA were included. Some results obtained with this CETP quantification system are shown in FIG. 2.

The invention claimed is:

1. A method of immunoenzymatically detecting the presence of cholesterol esterase transferring protein (CETP) in a biological or synthetic sample, wherein said method does not detect a CETP variant without a cholesterol ester binding motif, said method comprising:
   (a) obtaining said sample;
   (b) contacting said sample with a primary polyclonal antibody under conditions sufficient for said primary antibody to bind to CETP, wherein said primary antibody is raised against the polypeptide of SEQ ID NO: 5; and
   (c) enzymatically detecting the presence of said primary antibody from step (b), by contacting said sample and said primary antibody with a secondary antibody, wherein said secondary antibody comprises an enzymatic detection agent;
   wherein detection of said primary antibody indicates the presence of CETP comprising the cholesterol ester binding motif in said sample while not detecting CETP variants without the cholesterol ester binding motif; and
   wherein said method further comprises a positive control, wherein said positive control is glutathione-S-transferase (GST) fused to the polypeptide of SEQ ID NO: 4.

2. The method of claim 1, wherein said enzymatic detection agent is peroxidase.

3. The method of claim 1, wherein said primary antibody is polyclonal IgY.

4. The method of claim 1, wherein said sample is serum or plasma.

5. A method of immunoenzymatically detecting the presence of cholesterol esterase transferring protein (CETP) in a biological or synthetic sample, wherein said method does not detect a CETP variant without a cholesterol ester binding motif, said method comprising:
   (a) obtaining said sample;
   (b) contacting said sample with a primary polyclonal antibody under conditions sufficient for said primary antibody to bind to CETP, wherein said primary antibody is raised against the polypeptide of SEQ ID NO: 5; and
   (c) enzymatically detecting the presence of said primary antibody from step (b), by contacting said sample and said primary antibody with a secondary antibody, wherein said secondary antibody comprises an enzymatic detection agent;
   wherein detection of said primary antibody indicates the presence of CETP comprising the cholesterol ester binding motif in said sample while not detecting CETP variants without the cholesterol ester binding motif; and
   wherein said method further comprises a positive control, wherein said positive control is the polypeptide of SEQ ID NO: 5.

6. The method of claim 5, wherein said enzymatic detection agent is peroxidase.

7. The method of claim 5, wherein said primary antibody is polyclonal IgY.

8. The method of claim 5, wherein said sample is serum or plasma.

9. A method of determining the quantity of CETP in a biological or synthetic sample, wherein said method does not detect a CETP variant without a cholesterol ester binding motif, said method comprising:
   (a) obtaining said sample;
   (b) contacting said sample with a primary polyclonal antibody under conditions sufficient for said primary antibody to bind to CETP, and form a complex, wherein said primary antibody is raised against the polypeptide of SEQ ID NO: 5; and
   (c) quantitatively detecting the presence of said complex between CETP and said primary antibody with a secondary antibody, wherein said secondary antibody comprises an enzymatic detection agent, and wherein detection of said complex indicates the presence of CETP, and allows the quantification of CETP comprising said cholesterol ester binding motif in said sample while not detecting CETP variants without the cholesterol ester binding motif; and
   wherein said method further comprises a positive control, wherein said positive control is glutathione-S-transferase (GST) fused to the polypeptide of SEQ ID NO: 4.

10. The method of claim 9, wherein said enzymatic detection agent is peroxidase.

11. The method of claim 9, wherein said primary antibody is polyclonal IgY.

12. The method of claim 9, wherein said sample is serum or plasma.

13. A method of determining the quantity of CETP in a biological or synthetic sample, wherein said method does not detect a CETP variant without a cholesterol ester binding motif, said method comprising:
   (a) obtaining said sample;
   (b) contacting said sample with a primary polyclonal antibody under conditions sufficient for said primary antibody to bind to CETP, and form a complex, wherein said primary antibody is raised against the polypeptide of SEQ ID NO: 5; and
   (c) quantitatively detecting the presence of said complex between CETP and said primary antibody with a secondary antibody, wherein said secondary antibody comprises an enzymatic detection agent, and wherein detection of said complex indicates the presence of CETP, and allows the quantification of CETP comprising said cholesterol ester binding motif in said sample while not detecting CETP variants without the cholesterol ester binding motif; and
   wherein said method further comprises a positive control, wherein said positive control is the polypeptide of SEQ ID NO: 5.

14. The method of claim 13, wherein said enzymatic detection agent is peroxidase.

15. The method of claim 13, wherein said primary antibody is polyclonal IgY.

16. The method of claim 13, wherein said sample is serum or plasma.

17. A method of immunoenzymatically detecting the presence of cholesterol esterase transferring protein (CETP) in a biological or synthetic sample, wherein said method does not detect a CETP variant without a cholesterol ester binding motif, said method comprising:

(a) obtaining said sample;
(b) contacting said sample with a primary polyclonal antibody under conditions sufficient for said primary antibody to bind to CFTP, and form a complex, wherein said primary antibody is raised against the polypeptide of SEQ ID NO: 5;
(c) washing said complex from step (b);
(d) contacting said washed complex from step (c) with a secondary antibody under conditions sufficient for said secondary antibody to bind said primary antibody of said complex to form a primary-secondary antibody complex, wherein said secondary antibody comprises an enzymatic detection agent;

(e) washing said primary-secondary antibody complex from step (d); and (f) enzymatically detecting the presence of said secondary antibody from step (e), wherein detection of said secondary antibody indicates the presence of CETP containing the cholesterol ester binding motif in said sample while not detecting CETP variants without the cholesterol ester binding motif; and wherein said method further comprises a positive control, wherein said positive control is glutathione-S-transferase (GST) fused to the polypeptide of SEQ ID NO: 4.

18. The method of claim 17, wherein said enzymatic detection agent is peroxidase.

19. The method of claim 17, wherein said primary antibody is polyclonal IgY.

20. The method of claim 17, wherein said sample is serum or plasma.

21. A method of immunoenzymatically detecting the presence of cholesterol esterase transferring protein (CETP) in a biological or synthetic sample, wherein said method does not detect a CETP variant without a cholesterol ester binding motif, said method comprising:

(a) obtaining said sample;

(b) contacting said sample with a primary polyclonal antibody under conditions sufficient for said primary antibody to bind to CETP, and form a complex, wherein said primary antibody is raised against the polypeptide of SEQ ID NO: 5;

(c) washing said complex from step (b);

(d) contacting said washed complex from step (c) with a secondary antibody under conditions sufficient for said secondary antibody to bind said primary antibody of said complex to form a primary-secondary antibody complex, wherein said secondary antibody comprises an enzymatic detection agent;

(e) washing said primary-secondary antibody complex from step (d); and (f) enzymatically detecting the presence of said secondary antibody from step (e), wherein detection of said secondary antibody indicates the presence of CETP containing the cholesterol ester binding motif in said sample while not detecting CETP variants without the cholesterol ester binding motif; and wherein said method further comprises a positive control, wherein said positive control is the polypeptide of SEQ ID NO: 5.

22. The method of claim 21, wherein said enzymatic detection agent is peroxidase.

23. The method of claim 21, wherein said primary antibody is polyclonal IgY.

24. The method of claim 21, wherein said sample is serum or plasma.

* * * * *

SEQUENCE LISTING

```
<160> NUMBER OF SEQ ID NOS: 5

<210> SEQ ID NO 1
<211> LENGTH: 24
<212> TYPE: DNA
<213> ORGANISM: Oryctolagus cuniculus
<220> FEATURE:
<223> OTHER INFORMATION: Sense oligonucleotide, rabbit Cholesterol Ester
      Transfer Protein (CETP), mRNA.
<220> FEATURE:
<223> OTHER INFORMATION: From base 1391 to base 1414.  Located in the 3'
      end of exon 15, coding region.

<400> SEQUENCE: 1
tcatcaaccc cgagattatc actc                                          24

<210> SEQ ID NO 2
<211> LENGTH: 25
<212> TYPE: DNA
<213> ORGANISM: Oryctolagus cuniculus
<220> FEATURE:
<223> OTHER INFORMATION: Antisense oligonucleotide, rabbit Cholesterol
      Ester Transfer Protein, mRNA.
<220> FEATURE:
<223> OTHER INFORMATION: From base 1852 to base 1828.  Located in the
      non-encoding region of exon 16.

<400> SEQUENCE: 2
tcgtttactt gagaggcaga gagag                                         25

<210> SEQ ID NO 3
<211> LENGTH: 475
<212> TYPE: DNA
<213> ORGANISM: Artificial Sequence
<220> FEATURE:
<223> OTHER INFORMATION: 3' end of mRNA of the Cholesterol Ester
      Transfer Protein of rabbit, from base 1391 (exon 15) to base
      1852(exon 16), with a codon of vector pMosBlueT in
      its 5' end.
<220> FEATURE:
<223> OTHER INFORMATION: Subcloned fragment from vector pMosBlueT to
      vector pGex-2T. The first codon (GAT) corresponds to the
      codon transported from vector pMosBlueT during
      subcloning in vector pGex-2T.
<220> FEATURE:
<221> NAME/KEY: exon
<222> LOCATION: (4)..(42)
<223> OTHER INFORMATION: 3' exon 15.
<220> FEATURE:
```

-continued

```
<221> NAME/KEY: exon
<222> LOCATION: (43)..(117)
<223> OTHER INFORMATION: Exon 16 coding region.  The CETP stop codon
      (TAG) is found in base 496.

<400> SEQUENCE: 3 gat ctc ttc gaa atc atc aac ccc gag att atc act ctc gat ggc tgc      48 ctg ctg ctg cag atg gac ttc ggt ttt ccc aag cac ctg ctg gtg gat      96 ttc ctg cag agc ctg agc tag cagggagctg agacacaag acacgctgac         147 gtctccgccc atcggggtgg aggtcaggga gtgggtcgga ggacgggcga tggctcccaa   207
ctccttctgt cctgaagacc cctagcatga aagcagcata ccctgggcag gcatctggct  267
gagcggctaa gccactggtc aggacacctg cgtctagggt gctccggatc ccagctgcct  327
gctaacgtgc accctgggga gcagccgtgc tggttcccgc cagccacatc ggagacccag  387
actgaggtcc tggctcctgg ctttagcctg cccagtgagt ggcagctaaa tctctctggc  447
tgtctctctc tgcctctcaa gtaaacga                                     475

<210> SEQ ID NO 4
<211> LENGTH: 33
<212> TYPE: PRT
<213> ORGANISM: Artificial Sequence
<220> FEATURE:
<223> OTHER INFORMATION: Section corresponding to CETP in recombinant
      protein GST/CETPCOH. From residue Ile 464 to
      Ser 496.
<220> FEATURE:
<223> OTHER INFORMATION: Carboxyl terminal, cholesterol ester binding
      motive, responsible for the  transfer activity of
      cholesterol esters. Residues Phe 481, Leu 488, Phe
      491 and Leu 495 are shown below.
<220> FEATURE:
<221> NAME/KEY: HELIX
<222> LOCATION: (1)..(33)
<223> OTHER INFORMATION: High content of alfa helix structure;  M.W.
      3731.1 Daltons;  I.P. 3.99.

<400> SEQUENCE: 4

Ile Asn Pro Glu Ile Ile Thr Leu Asp Gly Cys Leu Leu Leu Gln Met
  1               5                  10                  15

Asp Phe Gly Phe Pro Lys His Leu Leu Val Asp Phe Leu Gln Ser Leu
                 20                  25                  30

Ser

<210> SEQ ID NO 5
<211> LENGTH: 12
<212> TYPE: PRT
<213> ORGANISM: Artificial Sequence
<220> FEATURE:
<223> OTHER INFORMATION: Synthetic sequence, translated from nucleotide
      sequence of the PCR product, obtained with
      oligonucleotides with 1 and 2 sequences.
<220> FEATURE:
<223> OTHER INFORMATION: From residue His 486 to Ser 496 +CyS in amino
      end.
<220> FEATURE:
<221> NAME/KEY: BINDING
<222> LOCATION: (2)..(12)
<223> OTHER INFORMATION: Carboxyl terminal, cholesterol ester binding
      motive, responsible for transfer activity of
      cholesterol esters. Residues Leu 488, Phe 491 and
      Leu 495 are shown below.
<220> FEATURE:
<221> NAME/KEY: HELIX
<222> LOCATION: (2)..(12)
<223> OTHER INFORMATION: High content of alpha-helix structure; M.W.
      1373.9 Daltons, I.P. 5.09, soluble in H2O pH 9.5.
```

```
<400> SEQUENCE: 5

Cys His Leu Leu Val Asp Phe Leu Gln Ser Leu Ser
1               5                   10
```